US008161581B2

(12) United States Patent
Park

(10) Patent No.: US 8,161,581 B2
(45) Date of Patent: Apr. 24, 2012

(54) THERAPEUTIC DEVICE OPERATIVELY CONNECTED TO A PROTECTIVE SUIT AND SUPPLYING HERB ESSENCE EVAPORATED FROM HEATED HERB TO THE PROTECTIVE SUIT

(76) Inventor: Joseph Min H. Park, Edmonds, WA (US)

( * ) Notice: Subject to any disclaimer, the term of this patent is extended or adjusted under 35 U.S.C. 154(b) by 1267 days.

(21) Appl. No.: 09/900,262

(22) Filed: Jul. 7, 2001

(65) Prior Publication Data

US 2002/0160057 A1 Oct. 31, 2002

(30) Foreign Application Priority Data

Apr. 25, 2001 (KR) ................................ 2001-22428

(51) Int. Cl.
*A61H 33/06* (2006.01)
*A61H 1/00* (2006.01)
*A61H 33/00* (2006.01)
*A61M 21/00* (2006.01)

(52) U.S. Cl. ................................ 4/529; 601/46; 607/83

(58) Field of Classification Search .................... 604/23, 604/24, 113, 115; 600/22; 5/941, 413 R, 5/421; 4/524–530; 601/16–19, 45, 49, 52, 601/55, 96; 607/100; 424/725
See application file for complete search history.

(56) References Cited

U.S. PATENT DOCUMENTS 2,507,815 A * 5/1950 Rice ................................ 604/23
3,946,733 A * 3/1976 Han ................................ 604/24
4,203,438 A * 5/1980 Shiu ................................ 604/24
4,680,822 A * 7/1987 Fujino et al. ...................... 5/421
4,747,841 A * 5/1988 Kuratomi et al. ............. 604/291
5,425,753 A * 6/1995 Wege et al. ..................... 607/83
5,632,768 A * 5/1997 Shimada ......................... 607/96
5,787,525 A * 8/1998 Sugihara et al. .................. 5/421
5,880,044 A * 3/1999 Shimiz .......................... 442/365
6,013,021 A * 1/2000 Lee .................................. 600/9
6,108,581 A * 8/2000 Jung ............................ 607/100
6,143,946 A * 11/2000 Docter ........................... 602/41
6,173,675 B1 * 1/2001 Licciardo .................... 119/28.5
6,272,697 B1 * 8/2001 Park ................................. 4/524
6,497,717 B1 * 12/2002 Daffer et al. .................... 607/83
(Continued)

FOREIGN PATENT DOCUMENTS

CH 683822 A5 * 5/1994
(Continued)

OTHER PUBLICATIONS

Sakurai et al., Machine Translation of JP06181878, Jan. 5, 2010.*

(Continued)

*Primary Examiner* — Theodore J Stigell
*Assistant Examiner* — William Carpenter

(57) ABSTRACT

A device for eliminating poisons and pollutants from the human body and for revitalizing cells includes a temperature controlled upper cover having a natural five primary substance stone coating layer, a temperature controlled lower mat having vibrators and a natural five primary substance stone coating layer, a herb essence supplier connected to the interior of space formed by the upper cover and the lower mat, and a negative ion producing air pump connected to the herb essence supplier for supplying negative ions. The device adjusts the temperature of a user in the interior space between the upper cover and the lower mat and discharges the poisons in the human body through perspiration holes on the skin by the action of the natural five primary substance stone and absorbed herbal essence.

16 Claims, 4 Drawing Sheets

U.S. PATENT DOCUMENTS

| | | | | |
|---|---|---|---|---|
| 6,666,813 | B1 * | 12/2003 | Ardizzone et al. | 600/9 |
| 6,745,411 | B1 * | 6/2004 | Kjonaas | 4/524 |

FOREIGN PATENT DOCUMENTS

| | | | | |
|---|---|---|---|---|
| CN | 1114329 | A | * | 1/1996 |
| JP | 05124973 | A | * | 5/1993 |
| JP | 06181878 | A | * | 7/1994 |
| JP | 09182776 | A | * | 7/1997 |
| KR | 2001111081 | | * | 12/2001 |
| WO | WO 02069880 | | * | 9/2002 |

OTHER PUBLICATIONS

Recihe et al., Heat Induced Transformation of Fossil Mastodon Ivory into Turquoise 'Odontolite'. Structural and Elemental Characterisation. 2000. Solid State Sciences 2, 625-636.*

Derwent. Ordinary-Temp. Far-Infrared Radiation Paint Abstract Translation. Derwent Information Ltd. 1997.*

Ha et al. In vivo characterization of sedative activites of Fossilia Mastodi Ossis. Jul. 29, 2006, Biological & Pharmaceutical Bulletin. vol. 29, pp. 1414-1417.*

David Pontoppidan, Family Discovers 10,000-Year-Old Mastodon Bones in Backyard. Nov. 10, 2009, Michigan Science No. 11.*

Reiche et al., From mastodon ivory to gemstone: The origin of turquoise color in odontolite, 2001, American Mineralogist, vol. 86, pp. 1519-1524.*

Park, Min-Ho, Translation of KIPO Patent Application 2001-22428, Apr. 25, 2001, KIPO, pp. 1-11.*

Seung-Sam Choi, Notice of Final Rejection for KIPO Patent Application 2001-0022428, KIPO, Jul. 13, 2004, p. 1.*

Gwak et al., Translation of KIPO Publication No. 2000-0001525, KIPO, Jan. 15, 2000, p. 1-9.*

Gwon-Tae et al., Translation of KIPO Publication No. 2000-0021510, KIPO, Dec. 26, 2000, p. 1-14.*

Se-Gu Lee, Translation of KIPO Publication No. 2000-0009864, KIPO, Sep. 15, 2000, p. 1-9.*

No Author Given, Report of Prior Art Search for KIPO Patent Application 2001-22428, KIPO, Jun. 17, 2003, p. 1.*

Lee, Ju-Gi, Notification of Reason for Refusal for KIPO Patent Applicaiton 2001-22428, KIPO, Dec. 20, 2003, p. 1-2.*

Buffington et al., "The Five Phases Paradigm and the Myers-BriggsType Indicator: Correspondence and Therapeutic Applicability," Medical Acupuncture, Spring/Summer 1998, vol. 10/No. 1. http://www.medicalacupuncture.com/aama_marf/journal/vol10_1/briggs.html.*

* cited by examiner

THERAPEUTIC DEVICE OPERATIVELY CONNECTED TO A PROTECTIVE SUIT AND SUPPLYING HERB ESSENCE EVAPORATED FROM HEATED HERB TO THE PROTECTIVE SUIT

CROSS REFERENCE TO RELATED ART

This application claims the benefit of Korean Patent Application No. 2001-22428, filed on Apr. 25, 2001, which is hereby incorporated by reference in its entirety.

BACKGROUND OF THE INVENTION

1. Field of the Invention

The present invention relates to a therapeutic and healing device, and particularly, to a device for eliminating harmful poisons and pollutants from the human body and for revitalizing cells, and to reproduce new activated cells and increase immunity against disease, thereby enhancing disease preventing capability and natural healing power.

2. Discussion of the Related Art

The rapid development of modern society has unfortunately come hand in hand with serious environmental damage, including but not limited to damage to the earth's air and water. The pollutants produced by mankind have affected not only the environment, but the human body as well.

The poisonous substances and pollutants that are accumulated in the human body include, but are not limited to: pollution poisons, climate poisons, food poisons, agricultural (farm product) chemical poisons, sea pollution poisons (marine products), polluted air and water, electromagnetic waves and stress affecting the human body, poisons due to abuse of medicines and so on. These pollutants damage the blood of the human and cause the destruction of the cells of the human body, and thereby are a major factor in causing diseases such as cancer and diabetes, and other health problems related to blood pressure, the thyroid gland, arthritis, etc.

If the above described poisons are absorbed into the human body and are allowed to pollute the blood, the blood becomes heated or cooled. This change in the blood causes the development of various health problems such as allergic dermatitis, atopic skin disease, asthma, cough, high blood pressure, damage to the thyroid gland, arthritis, arthralgia, neuralgia, etc. Furthermore, if these poisons are not removed from the body at a proper time, they cause the water in the human body to be polluted, and may cause rheumatism or congestion.

Rheumatism occurs when toxic substances are not discharged from the body through urine and stagnate within the body. Congestion occurs when poisons are not discharged and are collected in the human body. These conditions cause the following symptoms: swelling in the body; irregular digestion; gas; numbness in the hands and feet (commonly referred to as "falling asleep"); upset stomach; stiffness in the shoulders; and arthralgia and neuralgia in the legs and arms.

Moreover, portions of the human body may become discolored, turning black and blue as a result of traffic accidents or bruises. This is called extravasated blood or impure blood. This term applies to a situation where the blood is clogged. The extravasated blood or impure blood is not exhibited by X rays or biochemical tests, but it causes the corresponding portion of the human body to be painful for a long time. In addition, if the extravasated blood or impure blood is not discharged from the body, the following diseases are developed: cerebral thrombosis, neuralgia, and diseases involving the numbness of the hands and feet ("falling asleep"). As described above, if the pollutants are allowed to affect the blood and water of the human body and accumulate as poisonous substances in the human body, numerous kinds of diseases are developed.

Unfortunately, in the past there has been suggestions for a novel method for preventing numerous diseases that can be generated by the pollution of blood and water or the destruction of cells in the human body due to the general pollution of the environment, and for increasing the natural healing power against the diseases.

SUMMARY OF THE INVENTION

Accordingly, the present invention is directed to a therapeutic and healing device that substantially obviates one or more of the problems due to limitations and disadvantages of the related art.

It is an object of the present invention to provide a device for eliminating poisons and pollutants from the human body and for revitalizing cells, removing the sources of numerous diseases caused due to environmental pollution, thereby preventing disease as well as healing the body.

It is another object of the present invention to provide a device for: eliminating poisons and pollutants from the human body and for revitalizing cells; discharging poisons from the human body through perspiration pores on the skin; allowing the body to absorb herb components good for the human body through perspiration pores through which the poisons have been discharged, which allows the blood of the human body to be well circulated;

facilitating the secretion of the rheumatism and congestion in the blood through perspiration by removing the extravasated blood of the human body; adjusting to normal level the temperature of blood, and whereby the blood is purified, the cells and joints are cleaned, diseases are prevented, the immunity from disease is increased, and new activated cells are reproduced.

It is yet another object of the present invention to provide a device, to eliminate poisons and pollutants from the human body and to revitalize cells, that supplies in an easy manner herb essence good for the human body, thereby allowing polluted blood and cells to be revitalized.

The present inventors have proposed a device that allows the absorption of the herb essence into the human body by using a natural five primary substance stone coating layer. As a result, they have found that the pollutants in the human body can be removed and the cells therein can be revitalized.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To accomplish these and other objects of the present invention, there is provided a device for eliminating poisons and pollutants from the human body and for revitalizing cells, which comprises: an upper cover being adjustable in temperature, as a constant-temperature heating body and forming a natural five primary substance stone coating layer therein; a lower mat being adjustable in temperature, as a constant-temperature heating body and forming vibrators and the natural five primary substance stone coating layer therein; a herb essence supplying part connected to the interior of the space formed by the upper cover and the lower mat; a negative ion producing air pump connected to the herb essence supplying part, for supplying negative ions; and an air discharger connected to the interior of space formed by the upper cover and the lower mat, for discharging the internal air therein.

Preferably, the herb essence supplying part is comprised of a hot heat type herb essence supplier for evaporating herb essence by an internal electric hot wire to thereby supply the evaporated herb essence, a vibration type herb essence supplier for emitting the herb essence by the vibration of a vibration plate to supply the emitted herb essence, and a combustion type herb essence supplier for burning herbs by an internal electric hot wire to supply the perfume therein. In addition, the combustion type herb essence supplier may burn the herbs by the heating of the electric hot wire or by the heating of a heating ignition hole by virtue of an internal battery.

Each of the above-mentioned herb essence suppliers may be used with a plurality of herb essence supplier preferably in parallel with each other.

The natural five primary substance stone that is coated on the upper cover and the lower mat is a mixture of powders of about 10% to 20% by weight of a hematite, about 10% to 20% by weight of mastodon bones, about 30% to 40% by weight of an elvan, about 10% to 20% by weight of mica, and about 10% to 20% by weight of a loadstone.

In order to effectively induce the absorption of the herb essence and the discharge of the waste materials to/from a patient who lies in the space formed by the upper cover and the lower mat, the patient must put on a space uniform that is waterproof and coated with the natural five primary substance stone on the interior thereof. At this time, the air discharger of the herb essence supplying part is directly connected to the interior of the space uniform via a hose.

It is desirable that the herb essence is directly supplied to the portions of the body where the pain of the patient is severe. To this end, there is provided a pain relieving part that includes a substantially circular ceramic with a connecting hole connected to the air discharger of the herb essence supplying part. The five primary substance stone is coated on the portion of the bottom surface of the circular ceramic attached to the human body. Preferably, the pain relieving part is provided with a control box that adjusts the amount of the herb essence that is supplied.

Particularly, a feet finger-pressure curer and blood vessel stimulator is applied at various times, in order to apply the finger-pressure treatment to the patient's feet and stimulate the blood vessels on the feet. A ceramic body that corresponds to the shape of the sole of the foot is provided, and a plurality of protrusions is spaced at predetermined intervals on the portions with which the soles of the feet are contacted. Next, the natural five primary substance stone is coated on the upper portions of the plurality of protrusions. Both the feet finger-pressure curer and blood vessel stimulator may receive the herb essence from the herb essence supplying part.

Under the above construction, the device according to the present invention can adjust the temperature of the patient by operation of the upper cover and the lower mat that are adjustable in temperature, discharge the poisons in the human body, such as pollution poisons and foods poisons, through perspiration pores in the skin by the action of the natural five primary substance stone, and allow the absorption of herb components through the perspiration pores through which the poisons have been discharged, such that the blood of the human body is well circulated, the rheumatism and congestion in the blood are secreted through perspiration, the extravasated blood of the human body is removed, and the temperature of blood is adjusted to normal levels, whereby the blood is pure, the cells and joints are clean, diseases are prevented, the immunity from disease is increased, and new active cells are reproduced.

It is to be understood that both the foregoing general description and the following detailed description are exemplary and explanatory and are intended to provide a further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and, together with the description, serve to explain the principles of the invention.

DETAILED DESCRIPTION OF THE PREFERRED EMBODIMENTS

Figure 1A:
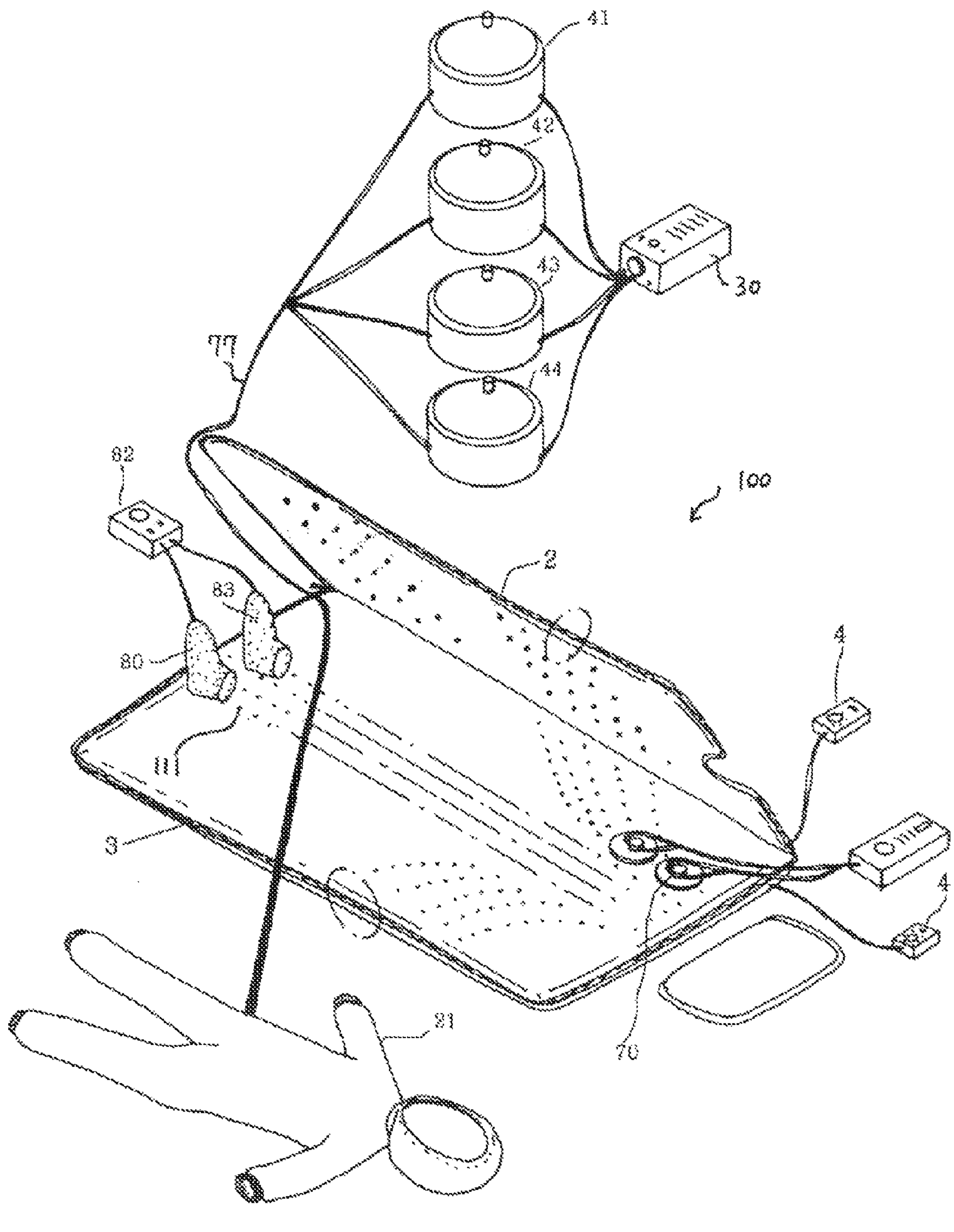
FIGS. 1*a* and 1*b* are perspective views of a device for eliminating poisons from human body and for revitalizing cells according to a preferred embodiment of the present invention.
Figure 1B:
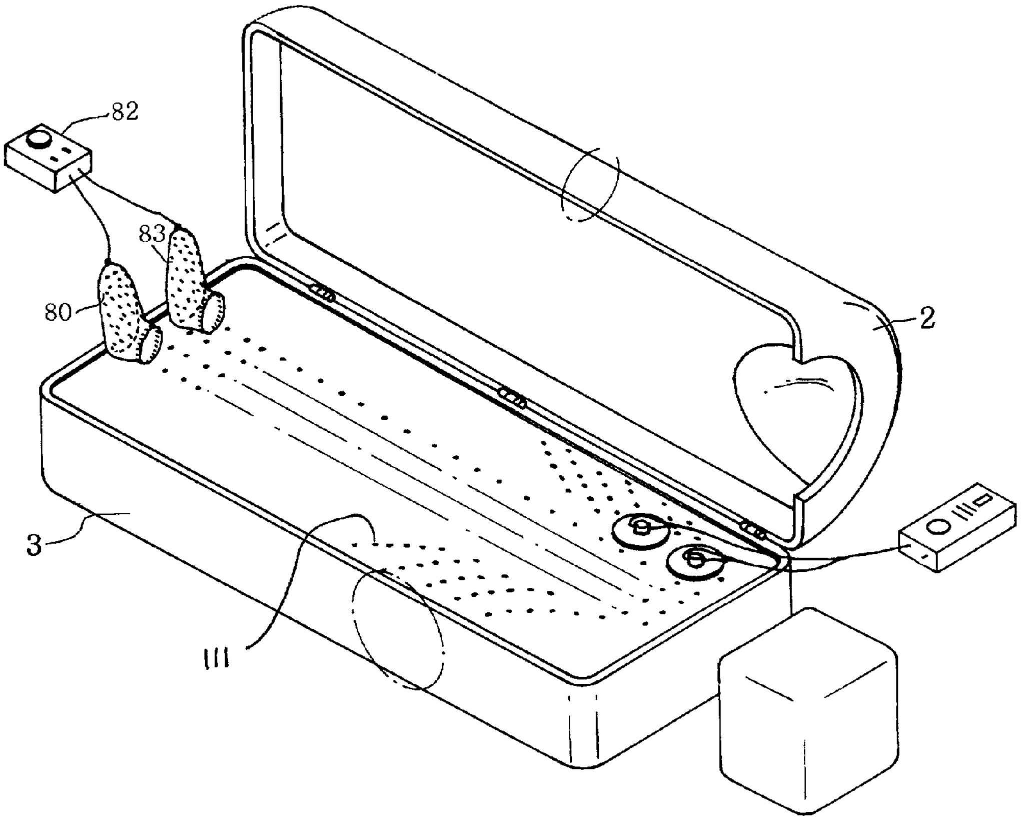

FIG. 1*a* is a perspective diagram of a device 100 for eliminating poisons from human body and for revitalizing cells according to the preferred embodiment of the present invention, wherein herb essence supplied from each one of herb essence suppliers 41 to 44 can be controlled by a valve disposed on each line. FIG. 1*b* is a diagram of an upper cover and a lower mat having an alternative shape according to the present invention.

According to FIG. 1*a*, the device 100 generally includes an upper cover 2, a lower mat 3 and a plurality of herb essence suppliers 41 to 44 connected to the lower mat 3 through a hose 77 to provide herb essence to the lower mat 3. The lower mat 3 has a plurality of protrusions 111 (better shown in FIG. 3) to stimulate various acupuncture points of the body. Although the preferred embodiment illustrates the lower mat 3 having the protrusions 111, the upper cover 2 may be equipped with the similar protrusions to stimulate the acupuncture points of the front of the body.

Figure 2:
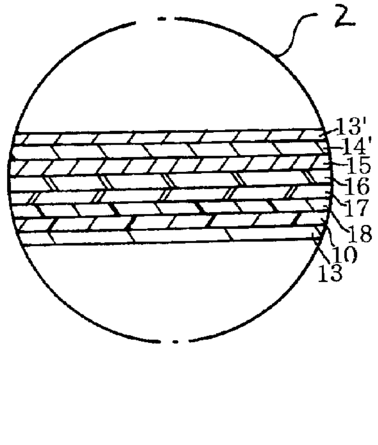
FIG. 2 is a cross-sectional schematic view of the internal structure of an upper cover of the device according to the present invention.
Figure 3:
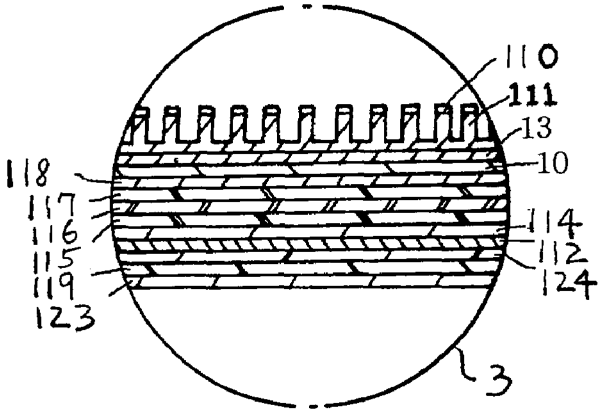
FIG. 3 is a cross-sectional schematic view of the internal structure of a lower mat of the device according to the present invention.

FIG. 2 is a schematic view of the internal structure of the upper cover of the device according to the present invention. FIG. 3 is a cross-sectional schematic view of the internal structure of the lower mat of the device according to the present invention. According to the preferred embodiment, the upper cover 2 is a mat of a constant-temperature heating body, which is laminated with cloth 13', preferably made of jacqard, sponge 14', an insulation material 15, a hot wire 16, an aluminum thin sheet 17, non-woven fabrics 18, a five primary substance stone 10 and Jagad cloth 13 in the named order. Preferably, the five primary substance stone is a mixture of powders of about 10% to 20% by weight of a hematite, about 10% to 20% by weight of mastodon bones, about 30% to 40% by weight of an elvan, about 10% to 20% by weight of mica, and about 10% to 20% by weight of a loadstone.

Referring to FIG. 3, the lower mat is laminated with cover cloth 113, five primary substance stone 110, non-woven fabrics 118, the first aluminum thin sheet 117, hot wire 116, insulation material 115, a buffering material 114, vibrators 112, the buffering material 124, the second aluminum thin sheet 119, and the cover cloth 123 in the named order.

As shown in FIG. 1*a*, the healing device 100 includes the upper cover 2 and the lower mat 3 are controlled by means of a temperature adjuster 4 such that their internal temperature can be adjusted up to about 40° C. to 60° C. In this way, the user who is disposed in the interior cavity defined between the upper cover 2 and the lower mat 3 is caused to perspire. Also, the upper cover 2 and the lower mat 3 are constructed in such a manner as to be protected from electromagnetic waves, and the natural five primary substance stone 10 emits remote infrared rays, thereby facilitating a high rate of perspiration.

The lower mat 3 is a constant-temperature heating body and a heated finger-pressure massager that emits infrared rays from the natural five primary substance stone 110 and applies the finger-pressure treatment on various portions of the body. The constant-temperature heating body serves to raise the internal temperature until the user perspires at a high rate. The heated finger-pressure massager includes a plurality of protrusions 111, preferably in the hundreds, and a plurality of vibrators 12, for example ten, that serve to tap, shake and massage the user's neck, shoulder, back and legs, thereby stimulating about 180 acupuncture spots located in the back of the human body. As a result, the user will experience increased blood circulation and faster opening of the perspiration pores. In addition, the user will feel refreshed and relaxed, and experience relief from pain.

According to the preferred embodiment of the present invention, the outlet of the essence suppliers 41 to 44 is in gaseous communication with the interior space of the device so that the user laying therein can absorb the herb essence.

As shown in FIGS. 1*a* and 1*b*, there is provided a number of protrusions 111 corresponding to the hundreds of acupuncture spots on the back of the human body. In order to stimulate the acupuncture spots and apply the finger pressure thereto, the protrusions 111 apply tapping, shaking and massaging to the spots by virtue of the operation of the vibrators 112, thereby increasing blood circulation and opening perspiration pores, such that the waste materials from the body can be easily discharged. Meanwhile, the herb fume introduced from the herb essence supplier 41 to 44 is moved along the blood vessels in the skin. When the skin cells are in a negative magnetic field under a temperature in a range of about 40° C. to 60° C., the ion passage is opened if any stimulation is applied to the acupuncture spots on the surface of the skins and thus, nutritive substances and waste materials are easily added and removed from the cells (in the direction of a negative electrode).

On the other hand, as shown in FIG. 1*a*, the user who is placed between the lower mat 3 and the upper cover 2 of the device 100 may put on a generally enclosed protective suit 21, in the form of an overall, that is preferably made of typical non-woven fabrics and waterproof coating material. The protective suit 21 is preferably coated with the natural five primary substance stone on the interior, so that the remote infrared rays are emitted therefrom. The temperature of the body is raised and the heat is collected, such that the user perspires and the discharged perspiration does not flow to the outside. As a result, the herb fume is well absorbed into the skin cells on the body when the herb essence and perfume are supplied.

FIGS. 4*a* to 4*d* are exemplary views of a herb essence supplier 41 having various shapes, as a component part of the present invention. The herb essence supplier 41 is connected to a negative ion producing air pump 30 shown in FIG. 1*a*. Each one of the herb essence supplier 41 to 44 preferably has the identical shape. The device 100 according to the present invention may be used with many different types of herbs. Due to the characteristics of such herbs, different types of herb essence suppliers may need to be used, as described below.

As schematically shown in FIG. 1*a*, the negative ion producing air pump 30 serves to produce negative ions and supply them to each one of the herb essence suppliers 41 to 44, such that the herb fume is transmitted to the protective suit 21 via a hose 77. The heating-type herb essence supplier 41 serves to carry out the heating of herb for evaporating the fragrant materials therefrom. The vibration-type herb essence supplier 42 serves to evaporate the herb essence by vibration. The combustion type herb essence suppliers 43 and 44 serve to burn the herb by the internal disposed electrically heated wire, and supply the perfume. Specifically, the first combustion type herb essence supplier 43 is used desirably for wet herbs, and the second combustion type herb essence supplier 44 is used desirably for dry herbs.

The negative ion producing air pump 30 changes ambient air into negatively charged air (i.e., negatively ionized air) and supplies the negatively charged air to each of the herb essence suppliers 41 to 44, such that the essence, perfume, and fumes (the materials generated upon combustion) of the herb can be transmitted to the protective suit 21 via the hose 77. The negative ion producing air pump 30 is provided with first and second discharging holes that are adapted to discharge air in turns of 1 to 5 minutes, wherein the time and strength of discharging can be controlled.

Figure 4A:
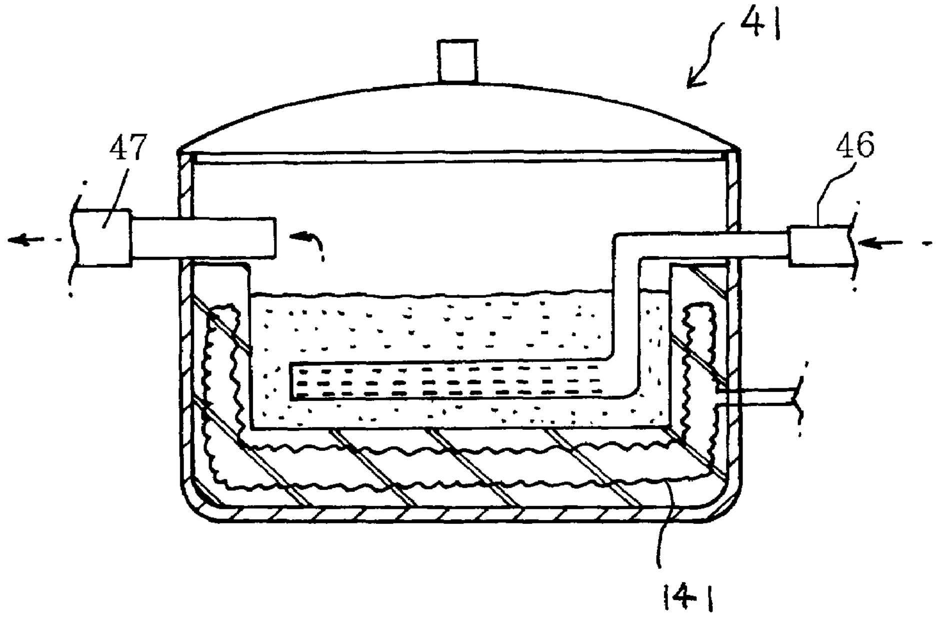
FIGS. 4*a* to 4*d* are exemplary views of a herb essence supplier having various shapes, as a component part of the present invention.

Referring to FIG. 4*a*, the hot heat type herb essence supplier 41 is provided to have a temperature controlled heating resistive wire 141. As the heat of the resistive wire increases the herb is heated and the herb essence is introduced. Preferably, the negatively ionized air is supplied from the air pump 30 and then discharged through an air discharging hole 47. The air is discharged with the evaporated herb essence. The essence supplier 41 is used for the kind of herb that is evaporated when heat is applied to the herb.

Figure 4B:
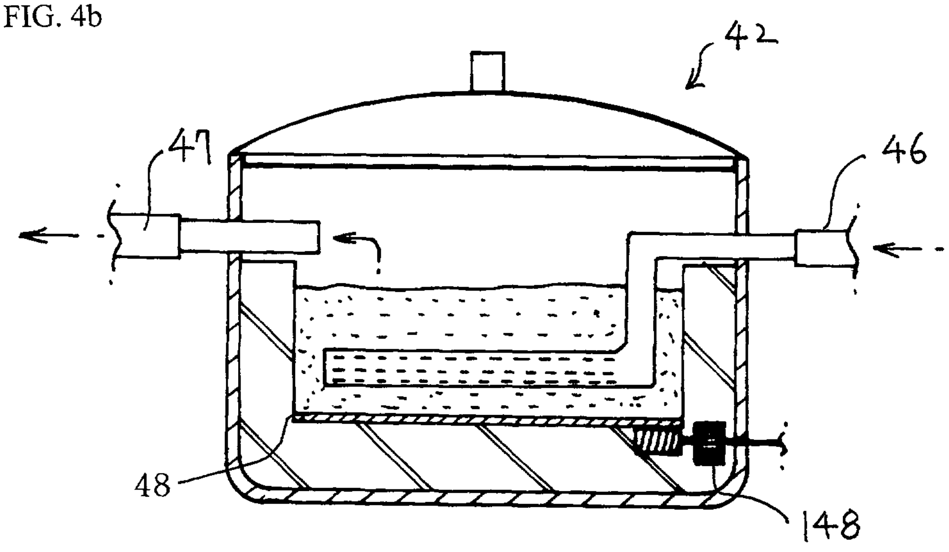

Referring to FIG. 4*b*, the vibration type herb essence supplier 42 is provided to emit the essence of herbs having good fragrant characteristics by the vibration of a vibration pin 48. The essence supplier 42 is used for herbs with strong fragrant characteristics and is thus easily emitted without heating. Preferably, a herb tank is vibrated in minute intervals, where the vibration sheet is vibrated with a small motor 148. The air with the negative ions produced from the air pump 30 is supplied and then discharged through the air discharging hole 47. As a result, the air is discharged with the herb essence, such that the perfume of the herb essence is transmitted to the protective suit 21.

Figure 4C:
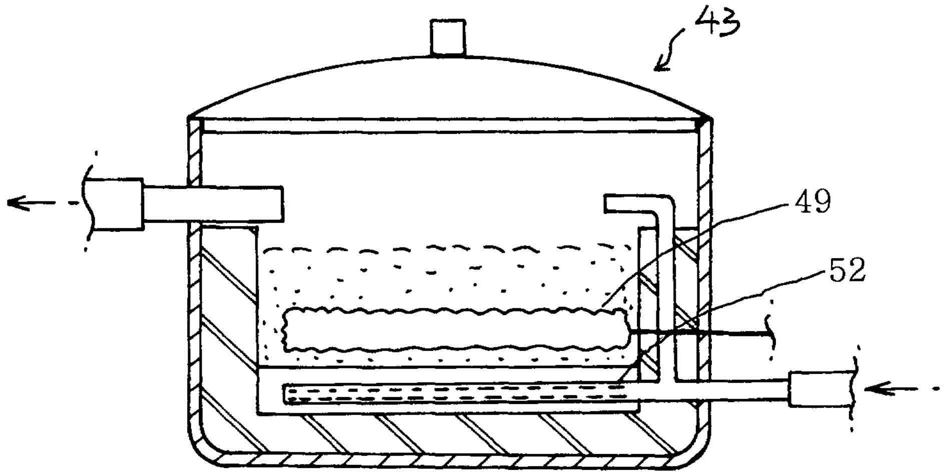

Referring to FIG. 4*c*, the first combustion type herb essence supplier 43 is provided to transmit positive fumes produced upon combustion of the herb. The essence supplier 43 is used, for example, in a similar manner in which incense is burned during meditation or during a memorial service in Asian countries. Preferably, the herb is thrown into the herb tank and then ignited by using an electrical heating wire 49, such that the herb is completely burned. The first combustion type herb essence supplier 43 has a strong combustion performance for the herb, and therefore, it can easily burn herbs containing significant amounts of moisture. Because the herb needs oxygen to burn, the negatively ionized air is supplied from the air pump 30 and then discharged through a plurality of air holes 52.

Figure 4D:
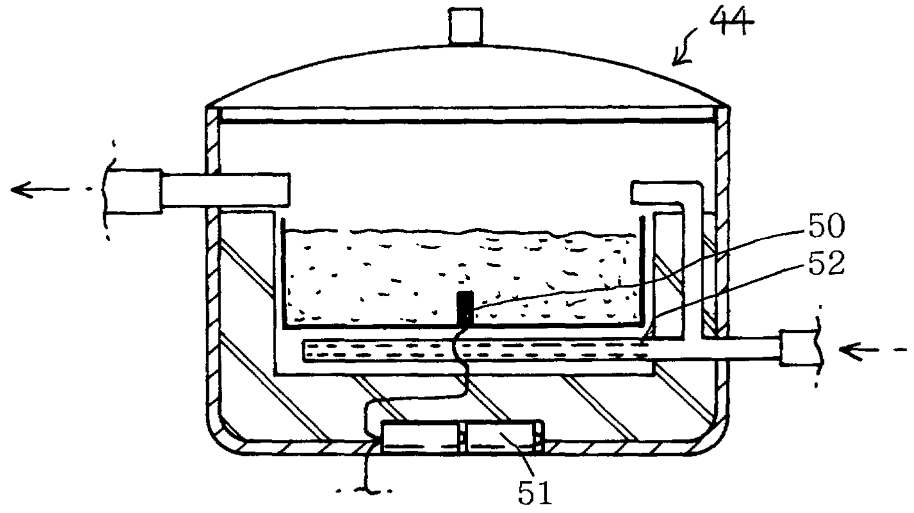

Referring to FIG. 4*d*, the second combustion type herb essence supplier 44 has the same principle as the first combustion type herb essence supplier 43, but it has an igniter 50

(similar to a lighter igniter) connected to a battery 51 to ignite the herb contained in the supplier. The supplier 44 is used for the kind of herb that is dried and completely burned by ignition. The herb used is pulverized, and it is burned continuously by ignition.

FIG. 1*a* denotes an attachment device 70 for attachment to body portions with enhanced or severe pain. The attachment device 70 is preferably made of circular ceramic material. The attachment device 70 is connected through respective connecting holes to the air discharger 47 of the herb essence supplier 41 to 44. The herb essence produced from the herb essence supplier 41 to 44 is supplied through the ceramics.

Preferably, the five primary substance stone is coated on the bottom surface of each of the attachment device 70 for adhering to user's body, such that the acupuncture stimulation occurs through the five primary substance stone. The several ceramics have the functions of tapping, shaking and massaging the painful portions of the body, thereby removing and pulling and otherwise stimulating the muscle and increasing pain relief.

FIG. 1*a* schematically shows feet finger-pressure massager and blood vessel stimulator 80 and 83, which massages the feet and applies finger-pressure treatment to the feet under the control of a control device 82. A plurality of natural five primary substance stone protrusions 83 serve to stimulate all acupuncture spots on, for example, the soles of feet.

The feet are generally regarded as a second body, since all structures of the human body are built in the inside of the soles in a contracted manner. From the viewpoint of Oriental medical science, all blood vessels in the body starts from the feet and/or end therein. Therefore, the spots suitable for acupuncture are collected on the soles of feet. All diseases can be healed only with the stimulation of the soles of feet, and the spots good for the protection of a heart disease and diseases for adult people exist in the soles of feet. Walking causes the soles of the feet to be stimulated, which is good for health. Applying the above principles, there is provided the feet finger-pressure massager 80 that is made of a ceramic body having the same size as the sole of the foot, thereby stimulating the five viscera and six entrails of the human body in an easy manner, such that various kinds of poisons accumulated in the body can be discharged and removed.

According to the present invention, a waste material air discharger may be employed, wherein an air vacuum pump serves to discharge air to the outside at a predetermined speed, and thus, the waste materials in an evaporated state in the inside of the space uniform are discharged to the outside, such that the interior of the space uniform can be filled with fresh negative ion air and herb substances.

Also, the patient may lie on a typical aluminum mat that serves as a protection film between the heating body of the upper cover and the lower mat, and which also serves to protect the space uniform.

As described above, a device according to the present invention exhibits the following excellent effects: increase of immunity against diseases; protection against diseases and aging; increased blood circulation due to the removal of waste materials in the body; relaxation of stiff muscle and elimination of pain; finger-pressure and massage effect; acupuncture treatment effect; body and hands and foot chill treatment by hot heating treatment effect; relax of nerves strained and body balancing adjustment by the stimulation of a nerve center; skin treatment including loose skin, pimples and other skin disease treatment and skin aging protection effect; an effect for treating the sources of all kinds of discs, lumbago, neuralgia and arthritis; an effect for treating an extravasated blood and a dropsical swelling due to accidents, bruises and sports injuries; an effect for treating the sources of chronic pain diseases; treatment for paralytics and patients requiring revival and physical treatment; symptom relieving effect for patients who suffer from neurosis, insomnia and a sense of instability; and an improvement effect in hormone secretion.

The foregoing embodiments and advantages are merely exemplary and are not to be construed as limiting the present invention. The description of the present invention is intended to be illustrative, and not to limit the scope of the claims. Many alternatives, modifications, and variations will be apparent to those skilled in the art. In the claims, mans-plus-function clauses are intended to cover the structure described herein as performing the recited function and not only structural equivalents but also equivalent structures.

What is claimed is:

1. A therapeutic device comprising:

an upper cover being adjustable in temperature in a range of 40° C-60° C. and forming a first coating layer comprising a mixture of powders of about 10% to 20% by weight of hematite, about 10% to 20% by weight of mastodon bones, about 30% to 40% by weight of an elvan, about 10% to 20% by weight of mica, and about 10% to 20% by weight of a loadstone;

a lower mat being adjustable in temperature in the range of 40° C-60° C. and forming a second coating layer comprising the mixture, the upper cover and the lower mat defining an interior space;

a plurality of herb essence suppliers externally disposed relative to and connected to the interior space formed by the upper cover and the lower mat, each of the plurality of herb essence suppliers having a discharge outlet connected to the interior space, wherein the plurality of herb essence suppliers comprise a heating-type herb essence supplier configured to heat herb and evaporate fragrant materials from the herb, a vibration-type herb essence supplier configured to evaporate herb essence by vibration, and a combustion-type herb essence supplier configured to supply perfume by burning herb;

an air pump connected to the plurality of herb essence suppliers for supplying air; and a protective suit sized to be worn by a human body and received within the interior space, wherein said protective suit is operatively connected to the plurality of herb essence suppliers via a hose.

2. The device of claim 1, wherein the heating-type herb essence supplier evaporates the herb essence by an electrical resistive wire.

3. The device of claim 1, wherein the heating-type herb essence supplier, the vibration-type herb essence supplier, and the combustion-type herb essence supplier are connected in parallel.

4. The device of claim 1, wherein the combustion-type herb essence supplier burns the herb by using either a resistive wiring or a heating ignition hole connected to an electrical source.

5. The device of claim 1, further comprising an attachment device made of a ceramic material and connected to the discharge outlet of the plurality of herb essence suppliers, wherein the mixture is coated on a bottom surface of the attachment device.

6. The device of claim 1, wherein the air pump provides negatively ionized air to the plurality of herb essence suppliers.

7. The device of claim 1, wherein the lower mat includes a plurality of protrusions for stimulating acupuncture points of a human body.

8. The device of claim 7, wherein the plurality of protrusions are coated with the mixture.

9. The device of claim 1, wherein the upper cover comprises an upper cover cloth, a sponge, a insulation material, a hot wire, an aluminum sheet, a non-woven fabric, and a lower cover cloth, and the lower mat comprises an upper cover cloth, a non-woven fabric, first and second aluminum sheets, a hot wire, an insulation material, a buffering material, vibrators, and a lower cover cloth.

10. The device of claim 9, wherein the upper cover clothes and the lower cover clothes of the upper cover and the lower mat comprise Jacquard cloth.

11. The device of claim 1, wherein various types of herbs are provided to the plurality of herb essence suppliers.

12. The device of claim 11, wherein the combustion-type herb essence supplier comprises a first supplier burning wet herbs and a second supplier burning dry herbs.

13. The device of claim 1, wherein the discharge outlet is connected to the interior space via a hose connected to the lower mat.

14. The device of claim 1, wherein the protective suit is made of non-woven fabrics and waterproof coating material.

15. The device of claim 14, wherein the protective suit is further coated with the mixture on the interior.

16. The device of claim 7, wherein the upper cover includes a plurality of protrusions for stimulating acupuncture points of the body.

* * * * *